US010702464B2

(12) United States Patent
Fondin et al.

(10) Patent No.: US 10,702,464 B2
(45) Date of Patent: *Jul. 7, 2020

(54) METHOD FOR TREATING HAIR FIBERS

(71) Applicant: L'OREAL, Paris (FR)

(72) Inventors: Thomas Fondin, Taverny (FR); Anne Sabbagh, Rueil Malmaison (FR)

(73) Assignee: L'OREAL, Paris (FR)

(*) Notice: Subject to any disclaimer, the term of this patent is extended or adjusted under 35 U.S.C. 154(b) by 484 days.

This patent is subject to a terminal disclaimer.

(21) Appl. No.: 15/584,472

(22) Filed: May 2, 2017

(65) Prior Publication Data
US 2017/0231887 A1 Aug. 17, 2017

Related U.S. Application Data

(60) Division of application No. 13/541,117, filed on Jul. 3, 2012, now Pat. No. 9,675,822, which is a continuation of application No. 11/097,167, filed on Apr. 4, 2005, now abandoned.

(60) Provisional application No. 60/571,922, filed on May 18, 2004.

(30) Foreign Application Priority Data

Apr. 2, 2004 (FR) ..................... 04 50667

(51) Int. Cl.
A61Q 5/00 (2006.01)
A61Q 5/04 (2006.01)
A61K 8/46 (2006.01)
A45D 1/04 (2006.01)
A45D 7/02 (2006.01)

(52) U.S. Cl.
CPC ............ A61K 8/46 (2013.01); A45D 1/04 (2013.01); A45D 7/02 (2013.01); A61Q 5/00 (2013.01); A61Q 5/04 (2013.01)

(58) Field of Classification Search
None
See application file for complete search history.

(56) References Cited

U.S. PATENT DOCUMENTS

| | | |
|---|---|---|
| 2,047,398 A | 7/1936 | Voss et al. |
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,463,264 A | 3/1949 | Graenacher et al. |
| 2,528,378 A | 10/1950 | Mannheimer |
| 2,723,248 A | 11/1955 | Wright |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,256,154 A | 6/1966 | Jenkins et al. |
| 3,472,243 A | 10/1969 | Wall et al. |
| 3,472,840 A | 10/1969 | Stone et al. |
| 3,632,559 A | 1/1972 | Matter et al. |
| 3,716,633 A | 2/1973 | Viout et al. |
| 3,810,977 A | 5/1974 | Levine et al. |
| 3,836,537 A | 9/1974 | Boerwinkle et al. |
| 3,874,870 A | 4/1975 | Green et al. |
| 3,917,817 A | 11/1975 | Vanlerberghe et al. |
| 3,929,990 A | 12/1975 | Green et al. |
| 3,944,904 A | 3/1976 | Hase |
| 3,946,749 A | 3/1976 | Papantoniou |
| 3,966,403 A | 6/1976 | Papantoniou et al. |
| 3,966,404 A | 6/1976 | Papantoniou et al. |
| 3,966,904 A | 6/1976 | Green et al. |
| 4,001,432 A | 1/1977 | Green et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,103,145 A | 7/1978 | Oliveri |
| 4,128,631 A | 12/1978 | Lundmark et al. |
| 4,131,576 A | 12/1978 | Iovine et al. |
| 4,137,208 A | 1/1979 | Elliott |

(Continued)

FOREIGN PATENT DOCUMENTS

| | | |
|---|---|---|
| CA | 714031 A | 7/1965 |
| CH | 353491 A | 4/1961 |

(Continued)

OTHER PUBLICATIONS

Abandoned U.S. Appl. No. 11/097,154, filed Apr. 4, 2005.
Copending U.S. Appl. No. 11/097,120, filed Apr. 4, 2005.
Copending U.S. Appl. No. 11/097,171, filed Apr. 4, 2005.
French Search Report for FR 04 50667, dated Nov. 30, 2004, Ex. B. Pelli-Wablat.
English language Abstract of FR 1 564 110, dated Apr. 18, 1969.
English language Abstract of FR 1 580 545, dated Sep. 5, 1969.
English language Abstract of FR 2 514 640, dated Apr. 22, 1983.
English language Abstract of FR 2 679 448, Jan. 29, 1993.
English language Abstract of EP 0 368 763, May 16, 1990.

(Continued)

Primary Examiner — Jyothsna A Venkat
(74) Attorney, Agent, or Firm — The Marbury Law Group, PLLC

(57) ABSTRACT

A hair fiber treating method not containing a fixing step, comprising, applying to the hair fibers at least one reducing composition, free of ceramide, comprising at least one reducing agent; and raising the temperature of the hair fibers using a heating iron at temperature of at least 60° C., wherein the temperature of the hair fibers are raised before or after the hair fibers are optionally rinsed.

20 Claims, No Drawings

(56) References Cited

U.S. PATENT DOCUMENTS

| | | | |
|---|---|---|---|
| 4,166,894 A | 9/1979 | Schaper | |
| 4,172,887 A | 10/1979 | Vanlerberghe et al. | |
| 4,189,468 A | 2/1980 | Vanlerberghe et al. | |
| 4,192,863 A | 3/1980 | Kondo | |
| 4,197,865 A | 4/1980 | Jacquet et al. | |
| 4,217,914 A | 8/1980 | Jacquet et al. | |
| 4,277,581 A | 7/1981 | Vanlerberghe et al. | |
| 4,282,203 A | 8/1981 | Jacquet et al. | |
| 4,289,752 A | 9/1981 | Mahieu et al. | |
| 4,308,878 A | 1/1982 | Silva | |
| 4,348,202 A | 9/1982 | Grollier et al. | |
| 4,349,532 A | 9/1982 | Vanlerberghe et al. | |
| 4,367,390 A | 1/1983 | Balleys et al. | |
| 4,381,919 A | 5/1983 | Jacquet et al. | |
| 4,422,853 A | 12/1983 | Jacquet et al. | |
| 4,452,261 A | 6/1984 | Bresak et al. | |
| 4,533,714 A | 8/1985 | Sebag et al. | |
| 4,579,732 A | 4/1986 | Grollier et al. | |
| 4,587,321 A | 5/1986 | Sebag et al. | |
| 4,591,610 A | 5/1986 | Grollier | |
| 4,608,250 A | 8/1986 | Jacquet et al. | |
| 4,749,732 A | 6/1988 | Kohl et al. | |
| 4,761,273 A | 8/1988 | Grollier et al. | |
| 4,777,040 A | 10/1988 | Grollier et al. | |
| 4,795,629 A | 1/1989 | Siuta-Mangano | |
| 4,812,307 A | 3/1989 | Siuta-Mangano | |
| 4,832,948 A | 5/1989 | Kondo | |
| 4,931,210 A | 6/1990 | Takahashi et al. | |
| 4,948,579 A | 8/1990 | Jacquet et al. | |
| 4,956,175 A | 9/1990 | Maignan et al. | |
| 4,970,066 A | 11/1990 | Grollier et al. | |
| 5,009,813 A | 4/1991 | Watanabe et al. | |
| 5,015,767 A | 5/1991 | Maignan et al. | |
| 5,046,516 A | 9/1991 | Barradas | |
| 5,085,860 A | 2/1992 | Junino et al. | |
| 5,106,612 A | 4/1992 | Maignan et al. | |
| 5,166,355 A | 11/1992 | Leistner et al. | |
| 5,196,189 A | 3/1993 | Jacquet et al. | |
| 5,237,071 A | 8/1993 | Leistner et al. | |
| 5,279,818 A | 1/1994 | Halloran et al. | |
| 5,334,377 A | 8/1994 | Junino et al. | |
| 5,346,691 A | 9/1994 | Raspanti | |
| 5,449,805 A | 9/1995 | Junino et al. | |
| 5,466,878 A | 11/1995 | Junino et al. | |
| 5,494,058 A | 2/1996 | Chan | |
| 5,570,708 A | 11/1996 | Samain | |
| 5,583,257 A | 12/1996 | Junino et al. | |
| 5,585,091 A | 12/1996 | Pelzer et al. | |
| 5,637,297 A | 6/1997 | Savaides et al. | |
| 5,643,557 A | 7/1997 | Eteve et al. | |
| 5,695,747 A | 12/1997 | Forestier et al. | |
| 5,708,151 A | 1/1998 | Mockli | |
| 5,801,244 A | 9/1998 | Raspanti | |
| 5,955,060 A | 9/1999 | Huglin et al. | |
| 5,957,140 A | 9/1999 | McGee | |
| 5,962,452 A | 10/1999 | Haase et al. | |
| 5,976,512 A | 11/1999 | Huber | |
| 5,983,903 A | 11/1999 | Nanba et al. | |
| 6,013,249 A | 1/2000 | Neill et al. | |
| 6,159,455 A | 12/2000 | Habeck et al. | |
| 6,235,271 B1 | 5/2001 | Luther et al. | |
| 7,976,831 B2 * | 7/2011 | Fondin | A61K 8/447 132/211 |
| 9,675,822 B2 * | 6/2017 | Fondin | A45D 1/04 |
| 2002/0146378 A1 | 10/2002 | Rose et al. | |
| 2005/0025736 A1 | 2/2005 | Jachowicz et al. | |
| 2011/0083695 A1* | 4/2011 | Abbasi | A45D 1/04 132/269 |

FOREIGN PATENT DOCUMENTS

| | | |
|---|---|---|
| DE | 2330956 A1 | 1/1974 |
| DE | 19726184 A1 | 12/1998 |
| DE | 19855649 A1 | 6/2000 |
| EP | 0122324 A1 | 10/1984 |
| EP | 0295780 A1 | 12/1988 |
| EP | 0299764 A2 | 1/1989 |
| EP | 0354835 A1 | 2/1990 |
| EP | 0368763 A1 | 5/1990 |
| EP | 0432000 A1 | 6/1991 |
| EP | 0514282 A1 | 11/1992 |
| EP | 0517104 A1 | 12/1992 |
| EP | 0518772 A1 | 12/1992 |
| EP | 0518773 A1 | 12/1992 |
| EP | 0570838 A1 | 11/1993 |
| EP | 0669323 A1 | 8/1995 |
| EP | 0681828 A1 | 11/1995 |
| EP | 0714954 A2 | 6/1996 |
| EP | 0775698 A1 | 5/1997 |
| EP | 0796851 A1 | 9/1997 |
| EP | 0863145 A2 | 9/1998 |
| EP | 0878469 A1 | 11/1998 |
| EP | 0893119 A1 | 1/1999 |
| EP | 0933376 A2 | 8/1999 |
| FR | 1085921 A | 2/1955 |
| FR | 1222944 A | 6/1960 |
| FR | 1400366 A | 5/1965 |
| FR | 1492597 A | 8/1967 |
| FR | 1530369 A | 6/1968 |
| FR | 1564110 A | 4/1969 |
| FR | 1580545 A | 9/1969 |
| FR | 1583363 A | 10/1969 |
| FR | 2162025 A1 | 7/1973 |
| FR | 2252840 A1 | 6/1975 |
| FR | 2265781 A1 | 10/1975 |
| FR | 2265782 A1 | 10/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2350384 A1 | 12/1977 |
| FR | 2357241 A2 | 2/1978 |
| FR | 2368508 A2 | 5/1978 |
| FR | 2413907 A1 | 8/1979 |
| FR | 2439798 A1 | 5/1980 |
| FR | 2505348 A1 | 11/1982 |
| FR | 2514640 A1 | 4/1983 |
| FR | 2535730 A1 | 5/1984 |
| FR | 2542997 A1 | 9/1984 |
| FR | 2679448 A1 | 1/1993 |
| GB | 339805 A | 6/1960 |
| GB | 922457 A | 4/1963 |
| GB | 1021400 A | 3/1966 |
| GB | 1199776 A | 7/1970 |
| GB | 1479786 A | 7/1977 |
| GB | 1546809 A | 5/1979 |
| GB | 1572626 A | 7/1980 |
| GB | 2197352 A | 5/1988 |
| GB | 2303549 A | 2/1997 |
| JP | 52-154529 A | 12/1977 |
| JP | 2000-256146 A | 9/2000 |
| JP | 2001-213741 A | 8/2001 |
| JP | 2002-356408 A | 12/2002 |
| JP | 2004-002459 A | 1/2004 |
| JP | 2004-026770 A | 1/2004 |
| LU | 75370 A1 | 2/1978 |
| LU | 75371 A1 | 2/1978 |
| WO | 95/01772 A1 | 1/1995 |
| WO | 95/15144 A1 | 6/1995 |

OTHER PUBLICATIONS

English language Abstract of JP 2002-356408, dated Dec. 13, 2002.
English language Abstract of JP 2004-26770, dated Jan. 29, 2004.
English language Abstract of JP 52-154259, dated Jun. 13, 1990.
English language Abstract of JP 2000-256146, Sep. 19, 2000.
English language Abstract of JP 2001-213741, Aug. 7, 2001.
English language Abstract of JP 2004-002459, Jan. 8, 2004.
English language Abstract of LU 75370, dated Feb. 8, 1978.
English language Derwent Abstract of FR 1 530 369, Jun. 21, 1968.

(56) References Cited

OTHER PUBLICATIONS

English language Derwent Abstract of FR 2 336 434, dated Jul. 22, 1977.
English language Derwent Abstract of FR 2 357 241, Feb. 3, 1978.
European Search Report for EP 05 30 0246, dated Aug. 17, 2005.
French Search Report of FR 04/50666, dated Dec. 6, 2004.
French Search Report of FR 04/50668, dated Mar. 31, 2005.
French Search Report of FR 04/50669, dated Dec. 3, 2004.
Office Action dated Aug. 12, 2009, in co-pending U.S. Appl. No. 11/097,120.
Office Action dated Jan. 6, 2009, in co-pending U.S. Appl. No. 11/097,120.
Office Action dated Jul. 23, 2008, in co-pending U.S. Appl. No. 11/097,120.
Office Action dated May 11, 2009, in co-pending U.S. Appl. No. 11/097,171.
Office Action dated Jan. 14, 2010, in co-pending U.S. Appl. No. 11/097,171.
Office Action dated Jun. 29, 2010, in co-pending U.S. Appl. No. 11/097,120.
Office Action dated May 12, 2011, in co-pending U.S. Appl. No. 11/097,120.
Final Office Action dated Dec. 14, 2011, in co-pending U.S. Appl. No. 11/097,120.
Final Office Action for co-pending U.S. Appl. No. 11/097,120, dated Dec. 2, 2016 (now abandoned).
Non-Final Office Action for co-pending U.S. Appl. No. 11/097,120, dated May 13, 2016 (now abandoned).
Final Office Action for co-pending U.S. Appl. No. 11/097,120, dated Nov. 20, 2015 (now abandoned).
Final Office Action for co-pending U.S. Appl. No. 11/097,120, dated Aug. 29, 2014 (now abandoned).
Final Office Action for co-pending U.S. Appl. No. 11/097,120, dated Jan. 13, 2014 (now abandoned).
Non-Final Office Action for co-pending U.S. Appl. No. 11/097,120, dated Jun. 10, 2013 (now abandoned).

* cited by examiner

METHOD FOR TREATING HAIR FIBERS

CROSS REFERENCE TO RELATED APPLICATIONS

This is a divisional of U.S. application Ser. No. 13/541,117, filed Jul. 3, 2012, which is a continuation of U.S. application Ser. No. 11/097,167, filed Apr. 4, 2005, which claims benefit of U.S. Provisional Application No. 60/571,922, filed May 18, 2004, and French Patent Application No. 0450667, filed Apr. 2, 2004, all of which are incorporated herein by reference.

Disclosed herein is a method for treating hair fibers by applying a reducing composition and then heating the hair with a heating iron.

The usual practice to permanently reshape hair comprises first opening the keratin disulfide bonds (cystine) with a composition comprising a reducing agent. The disulfide bonds are then re-formed, optionally after rinsing the hair, by applying to the hair, which has been straightened or placed beforehand under tension with suitable means such as cutlers or the equivalent, an oxidizing composition also called a fixing solution, so as to give the desired form to the hair. This method results in the waving of the hair, the uncurling of the hair, the backcombing of the hair, or the straightening of the hair.

Reducing compositions that can be used to carry out the first step of this method generally comprise compounds comprising a thiol group, such as thioglycolic acid, cysteine, cysteamine, thiolactic acid, and glycerol monothioglycolate.

The reducing agent concentration may be very high, often up to 15% by weight, relative to the total weight of the reducing composition.

Nevertheless, such a method may not be fully satisfactory. While it is very efficient to reshape the hair, it may cause great damage to the hair fibers.

Moreover, it has been suggested to raise the hair temperature between the reducing step and the fixing step by means of a heating iron.

For example, Patent Application No. JP 2000 256 146 describes a process to permanently reshape the hair, comprising the application of a cosmetic composition comprising from 2 to 11% reducing agents and from 0.2 to 4% diammonium dithiodiglycolate. After the reducing composition is applied, a heating iron is used at a temperature from 60 to 220° C.

Such a process nevertheless implies a post-iron fixing step as well, which increases the treatment time.

Moreover, the resulting shape is irreversible. The difference between the parts of the hair that have been treated and the hair roots is very noticeable as the hair regrows.

Finally, if the treatment is conducted on colored hair, it frequently causes the hair color to fade as a result of the treatment.

Thus, it would be desirable to provide a hair fiber treating method that compensates for at least one of the drawbacks of the prior art. For example, it would be desirable to provide a method that changes the hair fiber behavior while limiting the damage caused to the hair, controls the hair volume, and enhances at least one of the cosmetic benefits provided to the hair, for example, softness, shine and ease of combing, while also better preserving colored hair shades. Such a method would also ideally preserve the natural aspect of the hair so as to limit the so-called 'root effect', that is to say the contrast between the parts which have been treated and the roots, and also ideally reduce the hair fiber treating time and obtain long-lasting results.

The present inventors have found that it is possible to counteract at least one of the drawbacks of the prior art and to achieve at least one of the desirable results listed above, by carrying out a hair fiber treating method without fixing the hair, comprising applying to the hair fibers at least one reducing composition comprising at least one reducing agent chosen from compounds comprising at least one thiol group, wherein the at least one reducing agent is present in an amount of less than 3% by weight, relative to the total weight of the at least one reducing composition, and wherein the at least one reducing composition does not comprise an aminothiol compound or if the composition does comprise at least one aminothiol compound, it is present in an amount of less than 5% by weight, relative to the total weight of the at least one reducing composition, and raising the temperature of the hair fiber using a heating iron at a temperature of at least 60° C., wherein the temperature of the hair fiber is raised before or after the hair fibers are optionally rinsed.

Thus, disclosed herein is a method of treating hair fibers without fixing the hair, comprising:

applying to the hair fibers at least one reducing composition, free of ceramide, comprising at least one reducing agent chosen from thiols, wherein the at least one reducing agent is present in an amount of less than 3% by weight, relative to the total weight of the at least one reducing composition, provided that the at least one reducing composition does not comprise an aminothiol compound or if the at least one reducing composition does comprise at least one aminothiol compound, it is present in an amount of less than 5% by weight, relative to the total weight of the at least one reducing composition and applying to the hair fibers a heating iron at a temperature of at least 60° C. to raise the temperature of the fibers, wherein the temperature of the hair fiber is raised before or after the hair fibers are optionally rinsed.

As used herein, 'without fixing the hair' or 'without a hair-fixing step' means without any additional application of a composition comprising a chemical oxidizing agent, such as hydrogen peroxide or a bromate.

The at least one reducing composition may have a pH of less than or equal to 9, provided that the at least one reducing composition does not comprise an aminothiol compound.

In one embodiment, the at least one reducing composition does not comprise dithiodiglycolic acid or any salt thereof.

The at least one reducing composition may, for example, be applied onto wet and clean hair fibers.

As used herein, 'aminothiol compound' means a thiol comprising at least one NH moiety.

The thiols used as the at least one reducing agent may, for example, be chosen from aminothiols, such as cysteine and derivatives thereof, i.e., N-acetylcysteine, cysteamine and derivatives thereof, $C_1$-$C_4$ acylated derivatives thereof, such as N-acetyl cysteamine and N-propionyl cysteamine, and non-aminated thiols, such as thiolactic acid and esters thereof, such as glycerol monothiolactate, thioglycolic acid and esters thereof, such as glycerol and glycol monothioglycolate, and thioglycerol.

When the thiol comprises at least one carboxylic acid functional group, the thiol may be provided, if needed, in the form of at least one salt thereof, such as alkali metal or ammonium salts. In one embodiment, ammonium thioglycolate may be used. When the thiol has an amine moiety, the thiol may be provided, if needed, in the form of at least one salt thereof, such as aminothiol halogenides. In one embodiment, L-cysteine hydrochloride may be used.

Examples of aminothiols that may be used in the at least one reducing composition include sugar N-mercapto-alkyl amides, such as N-(mercapto-2-ethyl)-gluconamide, pantheteine, and N-(mercaptoalkyl)-ω-hydroxyalkyl amides such as those described in Patent Application No. EP-A-354 835 and N-mono- and N,N-dialkylmercapto 4-butyramides, such as those described Patent Application No. EP-A-368 763, aminomercaptoalkyl amides, such as those described Patent Application No. EP-A-432 000 and alkylaminomercaptoalkyl amides such as those described in Patent Application No. EP-A-514 282. Examples of non-aminated thiols that may be used include a mixture of hydroxy-2-propyl thioglycolate (2/3) and hydroxy-2 methyl-1 ethyl thioglycolate (67/33) described in Patent Application No. FR-A-2 679 448, β-mercaptopropionic acid and derivatives thereof, and thiomalic acid.

The total concentration of thiols in the at least one reducing composition is as follows:

when the at least one reducing composition comprises at least one aminothiol compound, the total concentration of thiols is less than 5% by weight, such as from 0.1 to 5% by weight, or further from 0.5 to 4% by weight, relative to the total weight of the at least one reducing composition, or when the at least one reducing composition does not comprise at least one aminothiol compound, the total concentration of thiols is less than 3% by weight, such as from 0.1% to 3% by weight and, further, for example, from 0.5% to 3% by weight relative to the total weight of the at least one reducing composition.

The pH of the at least one reducing composition may be adjusted by means of at least one agent chosen from alkaline agents and acidifying agents. The alkaline agents may, for example, be chosen from ammonia; organic amines, such as monoethanolamine, diethanolamine, triethanolamine, 1,3-propanediamine, and 2-amino-2-methyl-1-propanol; alkaline and ammonium carbonate or bicarbonate; organic carbonate, such as guanidine carbonate; alkaline hydroxide, such as soda. The acidifying agents may, for example, be chosen from hydrochloric acid, acetic acid, lactic acid, oxalic acid, and boric acid.

The at least one reducing composition may, for example, comprise at least one cosmetically acceptable solvent chosen, for example, from water, $C_1$-$C_6$ alcohols, for example, alkanols such as ethanol, propanol, and isopropanol; polyhydric alcohols, such as propyleneglycol, pentanediol and glycerine; benzyl alcohol; polyol ethers; $C_2$-$C_6$ esters; N-methylpyrrolidone (NMP); and $C_3$-$C_6$ cetones.

In order to improve at least some of the cosmetic properties of the present hair compositions, the at least one reducing composition may also comprise at least one cosmetic additive.

The at least one cosmetic additive may, for example, be chosen from volatile and non volatile, linear and cyclic silicones; cationic, non ionic, anionic and amphoteric polymers; peptides and derivatives thereof; protein hydrolyzates; waxes; swelling agents and penetrating agents; agents that are able to increase the efficiency of the at least one reducing agent, such as a $SiO_2$/polydimethylsiloxane mixture, dimethylisosorbitol, urea and derivatives thereof; anionic, cationic, non ionic, amphoteric, and zwitterionic surfactants; active agents for combating hair loss; anti-dandruff agents; natural and synthetic, associative and unassociative thickeners; suspension agents; sequestering agents; opacifying agents; dyes; sunscreen agents; vitamins and provitamins; fatty acids; fatty alcohols; mineral, vegetable, and synthetic oils; and fragrances and preserving agents.

As used herein, 'cationic polymer' means any polymer comprising cationic moieties and/or moieties that are ionizable to cationic moieties.

Examples of cationic polymers include polyamine, polyaminoamide and quaternary polyammonium type-polymers, which are known products.

Polyamine, polyaminoamide and quaternary polyammonium type-polymers suitable for use in the at least one reducing composition are those, for example, described in French Patent Nos. FR 2 505 348 and FR 2 542 997. These polymers may be chosen from at least one of the following:

(1) homopolymers or copolymers derived from acrylic or methacrylic acid esters or amides;

(2) cellulose ether derivatives comprising quaternary ammonium moieties described in French Patent No. FR 1 492 597;

(3) cationic cellulose derivatives, such as cellulose copolymers or cellulose derivatives grafted onto a water-soluble quaternary ammonium monomer, and described, for example, in U.S. Pat. No. 4,131,576, such as hydroxyalkylcelluloses, i.e. hydroxymethyl-, hydroxyethyl- and hydroxypropyl-cellulose, for example, grafted onto a methacryloylethyl-trimethylammonium salt, a methacrylamidopropyl-trimethylammonium salt or a dimethyldiallylammonium salt; for example, polyquaternium 10 (INCI denomination);

(4) other cationic polysaccharides described, for example, in U.S. Pat. Nos. 3,589,578 and 4,031,307, such as guar gums comprising trialkylammonium cationic moieties;

(5) polymers comprising piperazinyl moieties and linear or branched chain alkylene or hydroxyalkylene divalent groups, wherein the chains are optionally interrupted by at least one atom chosen from oxygen, sulphur, and nitrogen atoms or by aromatic or heterocyclic rings, as well as oxidation and/or quaternization products of these polymers. Such polymers are described, for example, in French Patent Nos. FR 2 162 025 and FR 2 280 361;

(6) water-soluble polyaminoamides, such as those, for example, described in French Patent Nos. FR 2 252 840 and FR 2 368 508;

(7) polyaminoamide derivatives, such as adipic acid/dialkylaminohydroxyalkyl dialkylene-triamine polymers, wherein the alkyl group comprises from 1 to 4 carbon atoms and is chosen, for example, from methyl, ethyl, and propyl groups, wherein the alkylene group comprises from 1 to 4 carbon atoms and may, for example, be an ethylene group. Such polymers are described, for example, in French Patent No. FR 1 583 363.

(8) polymers resulting from the reaction of a polyalkylene-polyamine comprising two primary amine moieties and at least one secondary amine moiety, with a dicarboxylic acid chosen from diglycolic acid and saturated aliphatic dicarboxylic acids comprising from 3 to 8 carbon atoms. The molar ratio between polyalkylene-polyamine and dicarboxylic acid ranging from 0.8:1 and 1.4:1; wherein the polyaminoamide resulting from such reaction is reacted with epichlorhydrine in a molar ratio of epichlorhydrine to secondary amine moiety of the polyaminoamide ranging from 0.5:1 to 1.8:1. Such polymers are described, for example, in U.S. Pat. Nos. 3,227,615 and 2,961,347;

(9) alkyldiallylamine and dialkyldiallylammonium cyclopolymers, such as dimethyldiallylammonium chloride homopolymer and diallyldimethylammonium chloride and acrylamide copolymers;

(10) quaternary diammonium polymers having a number average molecular weight typically ranging from 1000 to 100000, such as those described, for example, in French Patent Nos. FR 2 320 330, 2 270 846, 2 316 271, 2 336 434, and 2 413 907 and in U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020; hexadimethrine chloride (INCI denomination) commercially marketed by CHIMEX under the trade name MEXOMERE PO is another example;

(11) quaternary polyammonium polymers, such as those described in Patent Application No. EP-A-122 324;

(12) vinylpyrrolidone and vinylimidazole quaternary polymers, such as products commercially marketed under the trade names Luviquat® FC 905, FC 550 and FC 370 by B.A.S.F;

(13) polyamines such as Polyquart® H commercially marketed by HENKEL, registered under the name 'POLYETHYLENEGLYCOL (15) TALLOW POLYAMINE' in the CTFA dictionary; and

(14) methacryloyloxyalkyl($C_1$-$C_4$) trialkyl($C_1$-$C_4$)ammonium salt branched polymers, such as those commercially marketed under the trade names SALCARE® SC 92, SALCARE® SC 95 and SALCARE® SC 96 by ALLIED COLLOIDS.

Other cationic polymers that can be used include cationic proteins or cationic protein hydrolyzates, polyalkyleneimines, for example, polyethylene imines, polymers with vinyl pyridine or vinyl pyridinium moieties, polyamine and epichlorhydrine condensation products, quaternary polyureylenes, and chitin derivatives.

In one embodiment, the cationic polymers may be chosen from hexadimethrine chloride and dimethyldiallylammonium chloride homopolymers and copolymers.

As explained above, the at least one cosmetic additive may also be chosen from silicones.

Silicones that are suitable for use as the at least one cosmetic additive include polydimethylsiloxanes; quaternized polyorganosiloxanes, such as those described in French Patent Application No. FR 2 535 730; polyorganosiloxanes comprising alkoxycarbonylalkyl moieties modified with aminoalkyl moieties, such as those described in U.S. Pat. No. 4,749,732; polyorganosiloxanes, such as polydimethylsiloxane-polyoxyalkyl copolymer of dimethicone copolyol; a polydimethylsiloxane with stearoxy (stearoxy dimethicone) end groups; a polydimethylsiloxane-dialkylammonium acetate copolymer and a polydimethyl-siloxane polyalkylbetaine copolymer described in British Patent No. GB 2,197,352; and organo polysiloxanes modified by mercapto or mercaptoalkyl moieties such as those described in French Patent No. FR 1 530 369 and in European Patent Application No. EP 295 780.

Moreover, the at least one cosmetic additive may also be chosen from fatty acids and fatty alcohols.

The fatty acids may, for example, be chosen from $C_8$-$C_{30}$ carboxylic acids, such as palmitic acid, oleic acid, linoleic acid, myristic acid, stearic acid, lauric acid, and mixtures thereof.

The fatty alcohols may, for example, be chosen from $C_8$-$C_{30}$ alcohols, such as palmityl, oleyl, linoleyl, myristyl, stearyl, and lauryl alcohols.

The at least one reducing composition used in the method disclosed herein may be provided in a form chosen from an optionally thickened lotion, a cream, a gel, and a foam.

The method disclosed herein comprises applying the at least one reducing composition as defined above to hair fibers. Once the at least one reducing composition has been applied, it can be left on the hair fibers, optionally under a drying helmet, for a time period ranging from 5 to 60 minutes, for example, from 5 to 30 minutes.

As explained above, the method further comprises, after applying the reducing composition, optionally rinsing the hair fibers, then raising the temperature of the hair fibers, with a heating iron at a temperature of at least 60° C.

As used herein, 'iron' means any heating device which functions by contacting the hair fibers.

The end of the iron coming into contact with the hair may have various forms. It may, for example, have a plane surface, such as a flat iron. It may also have a rounded surface, such as a round iron.

The iron may be applied proceeding by successive separated touches for a few seconds or by gradually moving or sliding along hair locks.

All types of flat or round irons may be given as non limitative examples of suitable irons for use in the method disclosed herein, for example, those described in U.S. Pat. Nos. 4,103,145; 4,308,878; 5,983,903; 5,957,140; 5,494,058; and 5,046,516.

The hair fiber temperature may be raised at a temperature ranging from 60° C. to 250° C., such as from 120° C. to 220° C.

According to one embodiment, the hair fibers are not rinsed out before heat is applied in the form of the heating iron for raising the temperature of the hair fibers.

The method disclosed herein may also include partially pre-drying the hair fibers before raising the temperature of the hair fibers, so as to prevent any substantial steam development that might burn the hands of the hair stylist and the scalp of the user. This pre-drying may be done, for example, by using a hair drier, a hood, or it is also possible to let the hair dry naturally.

Further disclosed herein is a method as described herein to durably change the hair shape without excessively altering the hair color and/or without excessively damaging the hair fibers.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific example are reported as precisely as possible. Any numerical value, however, inherently contains certain errors necessarily resulting from the standard deviation found in their respective testing measurements.

The following examples are intended to illustrate the invention in a non-limiting manner.

EXAMPLES

The hair fiber treating method disclosed herein was carried out using a reducing composition.

Tested reducing compositions were as follows:

Reducing composition 1

| | |
|---|---|
| L-Cysteine | 1.4 g |
| MEXOMERE PO | 2.5 g |

-continued

| | |
|---|---|
| 2-amino-2-methyl-1-propanol | qs pH 9 |
| Demineralized water | qs 100 g |

Reducing composition 2

| | |
|---|---|
| Thioglycolic acid | 1.1 g |
| MEXOMERE PO | 2.5 g |
| 2-amino-2-methyl-1-propanol | qs pH 9 |
| Demineralized water | qs 100 g |

Reducing composition 3

| | |
|---|---|
| L-Cysteine | 1.4 g |
| Thioglycolic acid | 0.3 g |
| MEXOMERE PO | 2.5 g |
| 2-amino-2-methyl-1-propanol | qs pH 9 |
| Demineralized water | qs 100 g |

Reducing composition 4

| | |
|---|---|
| L-Cysteine | 1.4 g |
| 2-amino-2-methyl-1-propanol | qs pH 9 |
| Demineralized water | qs 100 g |

Tests were conducted on colored, naturally curling hair.

A reducing composition such as previously described was applied onto the hair and left on for 5 minutes.

The hair was then partially pre-dried using a hair drier before being treated using a flat iron heated to 180° C.

As a result, the hair fiber showed a good texture, a well controlled volume, a good respect of the color and a long term durability of the effects.

What is claimed is:

1. A method for treating hair fibers, the method comprising:
    applying to the hair fibers a reducing composition, free of ceramide, comprising at least one reducing agent present in an amount of less than about 3% by weight, relative to the total weight of the at least one reducing composition,
    wherein the at least one reducing agent is chosen from the group consisting of non-aminated thiols and salts of non-aminated thiols; and
    applying a heating iron to the hair fibers to raise the temperature of the hair fibers, wherein the heating iron has a temperature ranging from about 60° C. to about 250° C., and wherein the heating iron is applied before or after the hair fibers are optionally rinsed,
    wherein the method does not comprise a fixing step.

2. The method according to claim 1, wherein the reducing composition has a pH of less than or equal to about 9.

3. The method according to claim 1, wherein the reducing composition does not comprise dithiodiglycolic acid or any salt thereof.

4. The method according to claim 1, wherein the temperature of the heating iron ranges from about 120° C. to about 220° C.

5. The method according to claim 1, wherein the at least one reducing agent is present in an amount ranging from about 0.1% to about 3% by weight, relative to the total weight of the at least one reducing composition.

6. The method according to claim 5, wherein the at least one reducing agent is present in an amount ranging from about 0.5% to about 3% by weight, relative to the total weight of the at least one reducing composition.

7. The method according to claim 1, wherein the reducing composition is applied to wet and clean hair fibers.

8. The method according to claim 1, further comprising leaving the reducing composition on the hair fibers for a time period ranging from about 5 to about 60 minutes before applying a heating iron to the hair fibers.

9. The method according to claim 1, further comprising leaving the reducing composition on the hair fibers for a time period ranging from about 5 to about 30 minutes before applying a heating iron to the hair fibers.

10. The method according to claim 1, further comprising not rinsing the hair fibers after applying the reducing composition and before applying a heating iron to the hair fibers.

11. The method according to claim 1, further comprising partially pre-drying the hair fibers after applying the reducing composition and before applying a heating iron to the hair fiber.

12. The method according to claim 1, wherein the non-aminated thiols are chosen from the group consisting of thiolactic acid, esters of thiolactic acid, thioglycolic acid, esters of thioglycolic acid, and thioglycerol.

13. The method according to claim 1, wherein the at least one reducing agent is a non-aminated thiol in salt form.

14. The method according to claim 1, wherein the reducing composition comprises at least one solvent chosen from the group consisting of water, $C_1$-$C_6$ alcohols, polyhydric alcohols, benzyl alcohol, polyol ethers, $C_2$-$C_6$ esters, N-methylpyrrolidone (NMP), and $C_3$-$C_6$ ketones.

15. The method according to claim 14, wherein the $C_1$-$C_6$ alcohols are alkanols chosen from the group consisting of ethanol, propanol, and isopropanol.

16. The method according to claim 14, wherein the polyhydric alcohols are chosen from the group consisting of propyleneglycol, pentanediol, and glycerine.

17. The method according to claim 1, wherein the at least one reducing composition further comprises at least one cosmetic additive chosen from the group consisting of volatile silicones, non volatile silicones, linear silicones, cyclic silicones; cationic polymers, non ionic polymers, anionic polymers, amphoteric polymers; peptides, peptide derivatives; protein hydrolyzates; waxes; swelling agents, penetrating agents; agents that are able to increase the efficiency of the at least one reducing agent; anionic surfactants, cationic surfactants, non ionic surfactants, amphoteric surfactants, zwitterionic surfactants; active agents combating hair loss; anti-dandruff agents; natural thickeners, synthetic thickeners, associative thickeners, nonassociative thickeners; suspension agents; sequestering agents; opacifying agents; dyes; sunscreen agents; vitamins, provitamins; fatty acids; fatty alcohols; mineral oils, vegetable oils, synthetic oils; fragrances; and preserving agents.

18. The method according to claim 17, wherein the cationic polymers are chosen from the group consisting of hexadimethrine chloride, dimethyldiallylammonium chloride homopolymers, and dimethyldiallylammonium chloride copolymers.

19. The method according to claim 1, wherein the reducing composition is provided in a form chosen from the group consisting of an optionally thickened lotion, cream, gel, or foam.

20. A method for treating hair fibers to change the shape of the hair fibers without excessively altering the hair color and/or without excessively damaging the hair fibers, the method comprising:

applying to the hair fibers a reducing composition, free of ceramide, comprising at least one reducing agent present in an amount of less than about 3% by weight, relative to the total weight of the at least one reducing composition,
wherein the at least one reducing agent is chosen from the group consisting of non-aminated thiols and salts of non-aminated thiols; and
applying a heating iron to the hair fibers to raise the temperature of the hair fibers, wherein the heating iron has a temperature ranging from about 60° C., to about 250° C., and wherein the heating iron is applied before or after the hair fibers are optionally rinsed,
wherein the method does not comprise a fixing step.

* * * * *